(12) United States Patent
Lee

(10) Patent No.: US 11,819,223 B2
(45) Date of Patent: Nov. 21, 2023

(54) CUSTOMIZABLE SURGICAL BONE-CUTTING JIGSAW PUZZLE-TYPE GUIDE DEVICE AND CUSTOMIZABLE SURGICAL BONE-CUTTING GUIDE-TRACTION-SUCTION DEVICE

(71) Applicant: THE CATHOLIC UNIVERSITY OF KOREA INDUSTRY-ACADEMIC COOPERATION FOUNDATION, Seoul (KR)

(72) Inventor: Sang Hwa Lee, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 202 days.

(21) Appl. No.: 17/400,946

(22) Filed: Aug. 12, 2021

(65) Prior Publication Data

US 2021/0369289 A1    Dec. 2, 2021

Related U.S. Application Data

(62) Division of application No. 16/479,129, filed as application No. PCT/KR2018/007336 on Jun. 28, 2018, now Pat. No. 11,154,311.

(30) Foreign Application Priority Data

Dec. 15, 2017   (KR) .......................... 10-2017-0173125
Dec. 15, 2017   (KR) .......................... 10-2017-0173126

(51) Int. Cl.
*A61B 17/17*    (2006.01)
*B33Y 80/00*    (2015.01)
(Continued)

(52) U.S. Cl.
CPC ............ *A61B 17/17* (2013.01); *A61B 17/176* (2013.01); *A61B 34/10* (2016.02); *B33Y 80/00* (2014.12);
(Continued)

(58) Field of Classification Search
CPC ...................................................... A61B 17/176
See application file for complete search history.

(56) References Cited

U.S. PATENT DOCUMENTS

2011/0269100 A1    11/2011   Furrer et al.
2019/0076154 A1*   3/2019    Herzog .............. A61B 17/8071

FOREIGN PATENT DOCUMENTS

KR        10-0310123 B1    9/2001
KR     10-2008-0068657 A   7/2008
(Continued)

*Primary Examiner* — Sameh R Boles
(74) *Attorney, Agent, or Firm* — Bridgeway IP Law Group, PLLC; Sang Ho Lee; Hyun Woo Shin

(57) ABSTRACT

Provided is a customizable surgical bone-cutting jigsaw puzzle-type guide device. The customizable surgical bone-cutting jigsaw puzzle-type guide device includes: a main guide portion that includes a main contact surface lengthily formed along a required main incision line of a bone to be cut and shaped to be brought into contact with the bone, and a main guide surface forming a guide line together with the main contact surface along the same line as the main incision line and shaped to be brought into contact with a cutting blade for guiding the movement of the cutting blade during cutting of the bone; and a connection portion extending from the main guide portion and connected to a side of the bone such that the main guide portion may be supported on the bone, the connection portion being configured to be detachably attached to the side of the bone.

4 Claims, 14 Drawing Sheets

(51) Int. Cl.
*A61B 34/10* (2016.01)
*A61B 17/00* (2006.01)
(52) U.S. Cl.
CPC ............... *A61B 2017/00477* (2013.01); *A61B 2017/00526* (2013.01); *A61B 2034/108* (2016.02)

(56) References Cited

FOREIGN PATENT DOCUMENTS

| KR | 10-1478009 B1 | 1/2015 |
| KR | 10-2016-0033564 A | 3/2016 |
| KR | 10-1687053 B1 | 12/2016 |

\* cited by examiner (a)

(b)

(a)   (b)

CUSTOMIZABLE SURGICAL BONE-CUTTING JIGSAW PUZZLE-TYPE GUIDE DEVICE AND CUSTOMIZABLE SURGICAL BONE-CUTTING GUIDE-TRACTION-SUCTION DEVICE

CROSS-REFERENCE TO RELATED APPLICATIONS

This application is a divisional application of U.S. application Ser. No. 16/479,129 filed on Jul. 18, 2019, which is a national stage application under 35 USC § 371 of international application No. PCT/KR2018/007336 filed on Jun. 28, 2018, and claims priority under 35 USC § 119 to Korean application Nos. 10-2017-0173125 and 10-2017-0173126 filed on Dec. 15, 2017, the entire disclosures of which are incorporated herein by reference in their entirety.

TECHNICAL FIELD

The present disclosure relates to a customizable surgical bone-cutting jigsaw puzzle-type guide device, and more particularly, to a customizable surgical bone-cutting jigsaw puzzle-type guide device having an improved structure for rapidly and precisely cutting a bone of the body along a required incision line, coping with the anatomical difference between body parts of patients through patient-specific fabrication, and enabling fixation to the inside of the body by its own structure without using additional fixtures.

In addition, the present disclosure relates to a customizable surgical bone-cutting guide-traction-suction device, and more particularly, to a customizable surgical bone-cutting guide-traction-suction device having an improved structure for rapidly and precisely cutting a bone of the body along a required incision line, coping with the anatomical difference between body parts of patients through patient-specific fabrication, and preventing visual interference caused by bleeding or cooling water without using an additional device.

BACKGROUND ART

(1) Background Art 1

In general, medical procedures for cutting a portion of a bone for the purpose of treatment are performed by drawing an incision line on a portion to be treated, fixing a guide to a bone to be treated or an adjacent bone at a position corresponding to the incision line using fasteners such as screws for smooth movements of a cutting blade along the incision line, and then performing cutting.

However, this method for medical procedures causes the following problems.

In the related art, cutting is performed in a state in which a guide for guiding the movement of a cutting blade is fixed to a portion to be cut by securely attaching the guide to a surrounding bone using fasteners such as screws.

Therefore, since work for fixing the guide to the bone is additionally required, it is difficult to rapidly perform cutting and thus to provide high-quality medical services, and the portion (in particular, a portion which is anatomically weak) to which the guide is fixed may be damaged and thus may have to be additionally treated.

In addition, although such guides have to be provided according to different anatomical structures of different persons, guides provided according to the same standard are used in the related art for cutting, and thus it is difficult to provide patient-specific medical procedures and thus to rapid and precise medical procedures.

(2) Background Art 2

Furthermore, in general, when it is intended to cut a bone, an incision line A is drawn on a portion to be cut as shown in FIG. 12A, and then a cutter C is inserted to cut the bone along the incision line A as shown in FIG. 12B.

According to this method, however, a clinician has to cut a required portion based on his/her skill or experience while checking the incision line A with the naked eye, and thus, cutting may be performed not along the incision line A to cause unexpected damage to an anatomical structure. In addition, even when an assistant device is used for cutting, since the assistant device has to be operated in a narrow space in a narrow field-of-view condition together with a suction device for suctioning substances such as leaking blood, it is difficult to perform cutting. Accordingly, a clinician has to pay significant attention to cutting to handle these problems, and thus the fatigue of the clinician may increase.

DESCRIPTION OF EMBODIMENTS

Technical Problem

Technical Problem 1

Therefore, the present disclosure is proposed to solve the above-mentioned problems by providing a customizable surgical bone-cutting jigsaw puzzle-type guide device configured to enable precise and rapid cutting of a bone of the body along a required incision line.

Another objective of the present disclosure is to provide a customizable surgical bone-cutting jigsaw puzzle-type guide device configured to be securely fixed to the inside of the body by its own structure without using additional tools.

Another objective of the present disclosure is to provide a customizable surgical hone-cutting jigsaw puzzle-type guide device configured to be fabricated in a patient-specific manner to cope with different anatomical structures of persons.

Another objective of the present disclosure is to provide a customizable surgical bone-cutting jigsaw puzzle-type guide device having a block type design such that when cutting is necessary at a plurality of portions, precise cutting may be performed along cutting lines of pre-designed blocks.

Technical Problem 2

The present disclosure is proposed to solve the above-mentioned problems by providing a customizable surgical bone-cutting guide-traction-suction device configured to enable precise and rapid cutting of a bone of the body along a required incision line and prevent visual interference caused by bleeding without using an additional tool.

Another objective of the present disclosure is to provide a customizable surgical bone-cutting guide-traction-suction device configured to be fabricated in a patient-specific manner to cope with different anatomical structures of persons.

Solution to Problem

To achieve the objectives, according to an embodiment of the present disclosure, a customizable surgical bone-cutting jigsaw puzzle-type guide device includes: a main guide portion that includes a main contact surface and a main guide surface, the main contact surface being lengthily formed along a required main incision line of a bone which is an object to be cut and being shaped to be brought into contact with the bone, the main guide surface forming a guide line between the main contact surface and the main guide surface along a same line as the incision line and being shaped to be brought into contact with a cutting blade for cutting the body to guide a movement of the cutting blade when the cutting blade cuts the bone; and a connection portion that extends from the main guide portion and is configured to be connected to a side of the bone such that the main guide portion is supported on the bone, the connection portion being configured to be detachably attached to the side of the bone.

To achieve the objectives, according to an embodiment of the present disclosure, a customizable surgical bone-cutting guide-traction-suction device includes: a body portion that includes a contact surface shaped to be brought into contact with a bone which is an object to be cut, a guide surface forming a guide line between the contact surface and the guide surface along a same line as an incision line of the object and shaped to be brought into contact with a cutting blade to guide a movement of the cutting blade when the cutting blade cuts the bone, and an internal empty space, the guide surface including a plurality of holes communicating with the empty space; and a connection portion connected to the body portion to handle the body portion placed in a human body from an outside of the human body and discharge unnecessary substances to the outside of the human body through the holes and the empty space of the body portion.

Advantageous Effects of Disclosure

Inventive Effect 1

The customizable surgical bone-cutting jigsaw puzzle-type guide device provides merits in that a cutting portion may be precisely cut as a cutting blade is guided by the main guide portion along a required incision line, and the connection portion extending from the main guide portion may be installed in the body without using additional fixtures for rapid and precise medical procedures and high-quality medical services.

In addition, according to an embodiment in which the customizable surgical bone-cutting jigsaw puzzle-type guide device is fabricated in a customized manner by a 3D printing method, a customized shape suitable for the structure of a bone which varies by person may be easily formed by the 3D printing method, and thus patient-specific medical procedures may be provided for high-quality medial services.

Inventive Effect 2

According to the customizable surgical bone-cutting guide-traction-suction device of the present disclosure, the body portion may be supported on a bone, and the bone may be cut while moving a cutting blade along the guide surface of the body portion, thereby preventing cutting misaligned with a required incision line, enabling rapid and precise medical procedures, and reducing clinician's fatigue. Therefore, high-quality medical services may be provided, and the effect of treatment may be improved Furthermore, in the customizable surgical bone-cutting guide-traction-suction device of the present disclosure, an empty space is formed in the body portion, and a plurality of holes communicating with the empty space are formed in the guide surface of the body portion such that unnecessary substances such as leaking blood may be suctioned using the structure of the customizable surgical bone-cutting guide-traction-suction device without using an additional tool in the narrow oral cavity, and the view of a clinician may not be blocked by bleeding. Therefore, clinicians may perform medical procedures more easily and precisely.

In addition, according to an embodiment in which the customizable surgical bone-cutting guide-traction-suction device is fabricated in a customized manner by a 3D printing method, a customized shape suitable for the structure of a bone which varies by person may be easily formed by the 3D printing method, and thus patient-specific medical procedures may be provided for high-quality medial services.

BEST MODE (Description of Customizable Surgical Bone-Cutting Jigsaw Puzzle-Type Guide Device)

Hereinafter, a customizable surgical bone-cutting jigsaw puzzle-type guide device will be described in detail according to an embodiment of the present disclosure with reference to the accompanying drawings.

Figure 1:
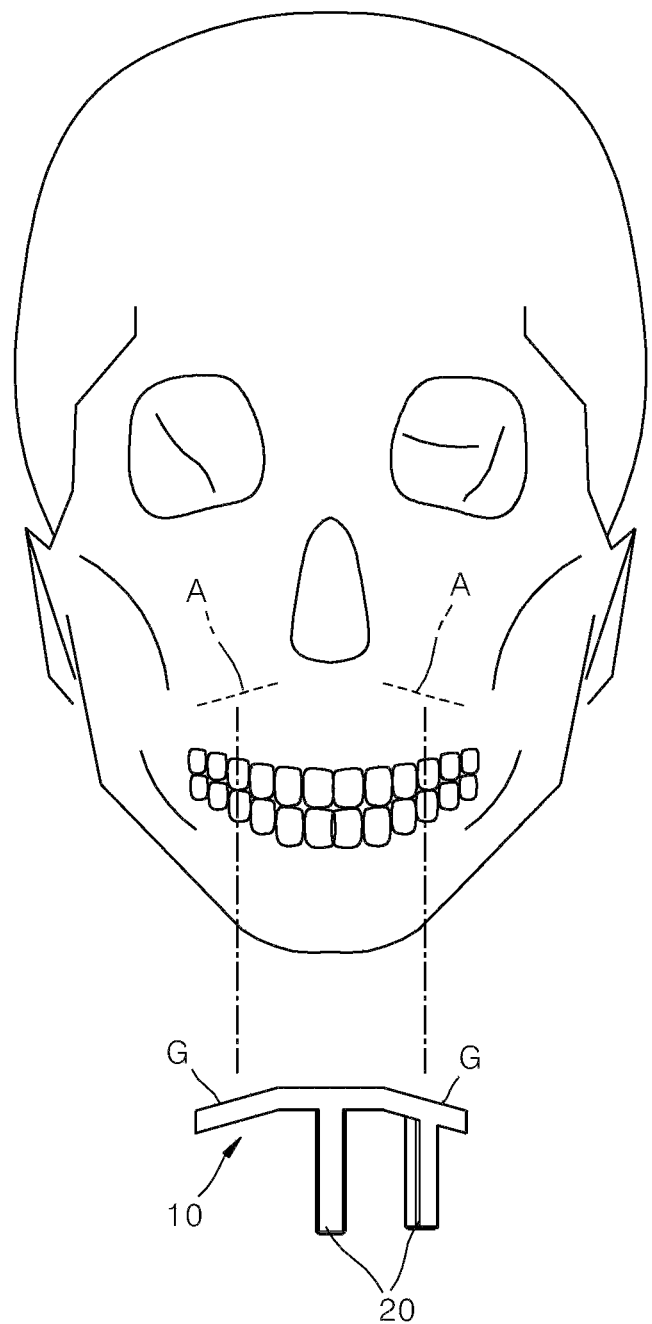
FIG. 1 is a front view illustrating the structure and an example use of a customizable surgical hone-cutting jigsaw puzzle-type guide device according to an embodiment of the present disclosure.
Figure 2:
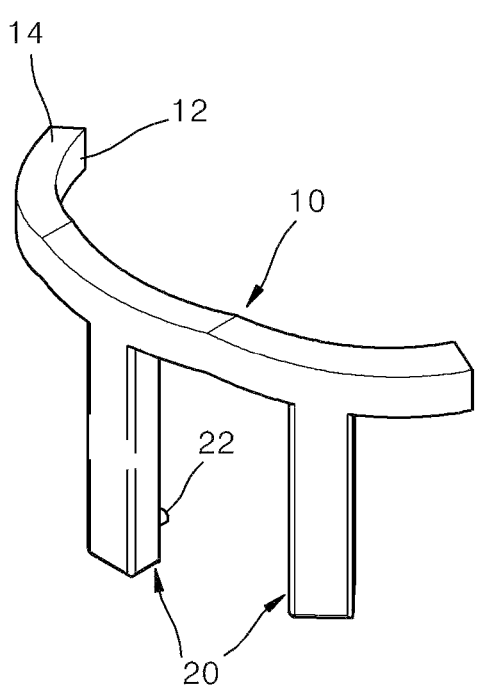
FIG. 2 is a perspective view according to the embodiment of the present disclosure.
Figure 3:
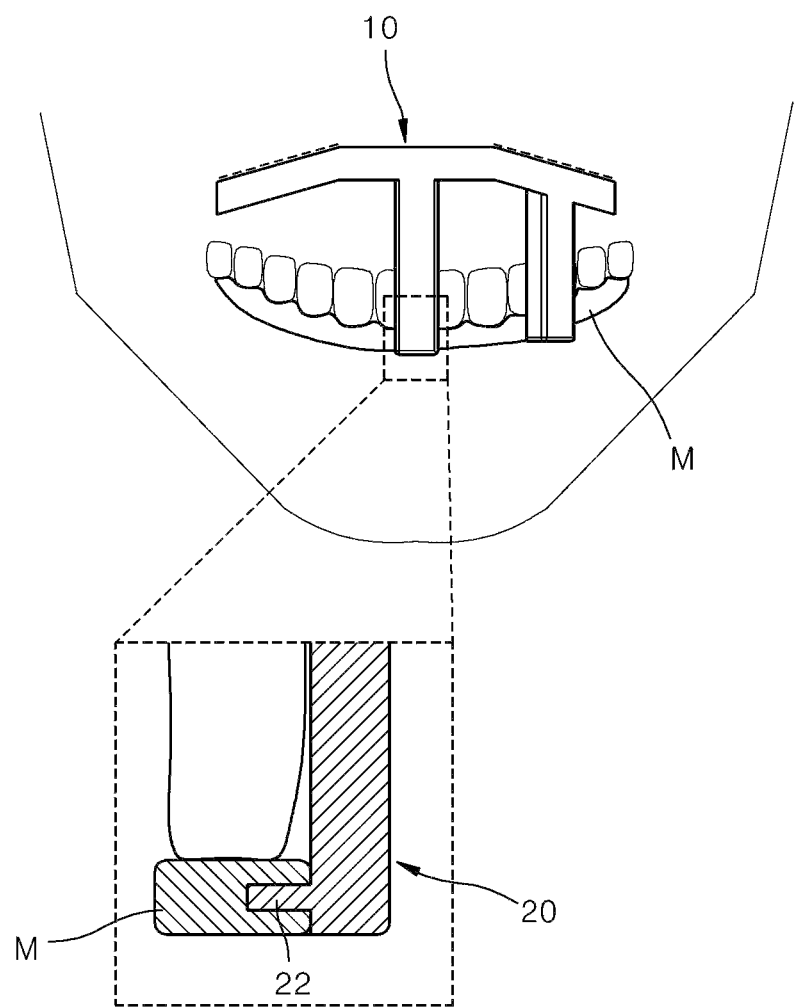
FIG. 3 is a view illustrating an installation structure according to the embodiment of the present disclosure.

FIG. 1 is a front view illustrating the structure and an example use of a customizable surgical bone-cutting jigsaw puzzle-type guide device according to an embodiment of the present disclosure, FIG. 2 is a perspective view according to the embodiment of the present disclosure, and FIG. 3 is a view illustrating an installation structure according to the embodiment of the present disclosure.

As shown in the drawings, the customizable surgical bone-cutting jigsaw puzzle-type guide device according to the embodiment of the present disclosure is for guiding a cutting operation in which a cutting tool such as a cutter is used to, for example, cut the upper jawbone to correct twisting or protruding of the upper jawbone. The customizable surgical bone-cutting jigsaw puzzle-type guide device includes a main guide portion 10 and connection portions 20.

As shown in FIG. 2, the main guide portion 10 includes: a main contact surface 12 configured to be brought into contact with a bone; and a main guide surface 14 forming a curved guide line G along the main contact surface 12 and configured to guide a cutting blade.

As shown in FIG. 1, the main contact surface 12 is formed such that the main contact surface 12 extends lengthily along required main incision lines A of a bone to be cut, and the guide line G is provided between the main guide surface 14 and the main contact surface 12 along the same line as the main incision lines A.

The main guide portion 10 is shaped such that the main guide surface 14 may guide the movement of a cutting blade in a state in which the main contact surface 12 is fixed to the inside of the body, and thus, for example, a maxillofacial bone may be precisely cut along the main incision lines A as shown in FIG. 1.

The connection portions 20 extend from the main guide portion 10 and are configured to be connected to a side of a bone such that the main guide portion 10 may be supported by the bone as shown in FIG. 3. The connection portions 20 may be detachably attached to the side of the bone by their own structure.

The customizable surgical bone-cutting jigsaw puzzle-type guide device of the embodiment of the present disclosure provides merits in that a cutting portion may be precisely cut while a cutting blade is guided by the main guide portion 10 along a required incision line, and the connection portions 20 extending from the main guide portion 10 may be attached to the inside of the body without using additional fixtures for rapid and precise medical procedures and high-quality medical services.

In the current embodiment, the bone to be cut may be the upper jawbone, and the side of the bone to which the connection portions 20 are attached may correspond to a medical guide M coupled to teeth in the oral cavity. Examples of the medical guide M may include a surgical stent for implantation and a bracket fixed to teeth for upper or lower jawbone treatment.

As shown in FIG. 3, the connection portions 20 include coupling bosses 22 configured to be press fitted into holes of the medical guide M.

In the current embodiment having the above-described configuration, the main guide portion 10 configured to guide the movement of a cutting blade may be fixed in the oral cavity by its own structure without using additional fixtures such that the speed and precision of medical procedures may be improved.

In addition, although the main guide portion 10 and the connection portions 20 may be formed by various methods, the main guide portion 10 and the connection portions 20 may be formed in one piece by a 3D printing method to have a shape corresponding to the shape of an object to be cut which varies by person.

According to the current embodiment having the above-described configuration, a customized shape suitable for the shape of the upper jawbone which varies by person may be easily formed by a 3D printing method, and thus patient-specific medical procedures and high-quality medical services may be provided.

Figure 4:
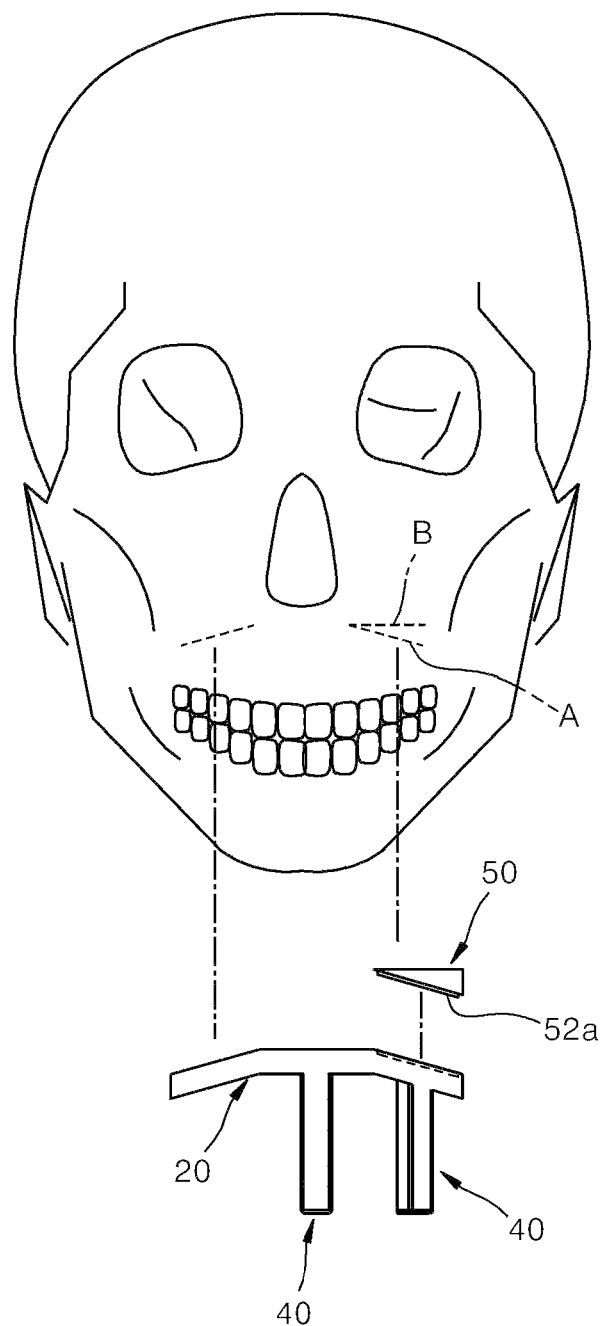
FIG. 4 is a front view illustrating the structure and an example use of a customizable surgical bone-cutting jigsaw puzzle-type guide device according to another embodiment of the present disclosure.
Figure 5:
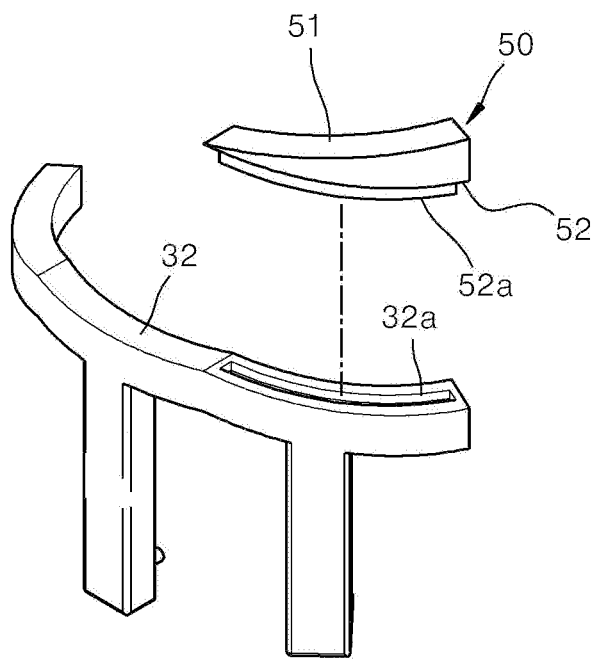
FIG. 5 is an exploded perspective view according to the other embodiment of the present disclosure.
Figure 6:
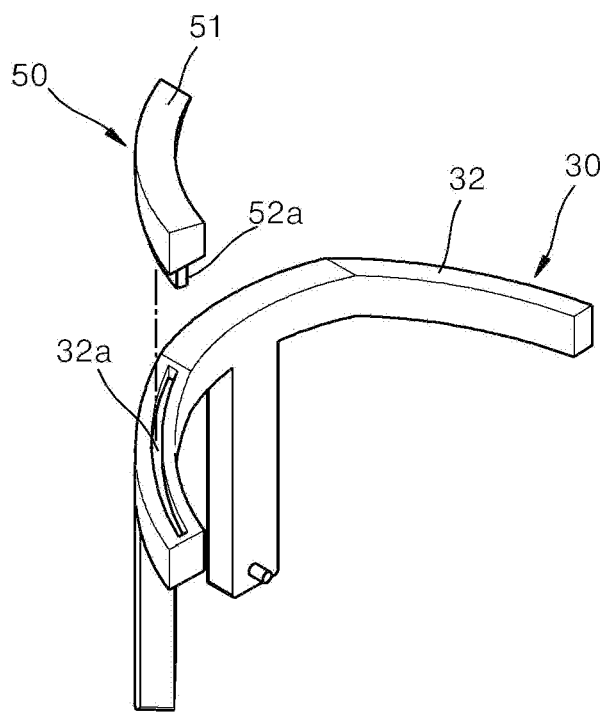
FIG. 6 is an exploded perspective view at a different angle according to the other embodiment of the present disclosure.
Figure 7:
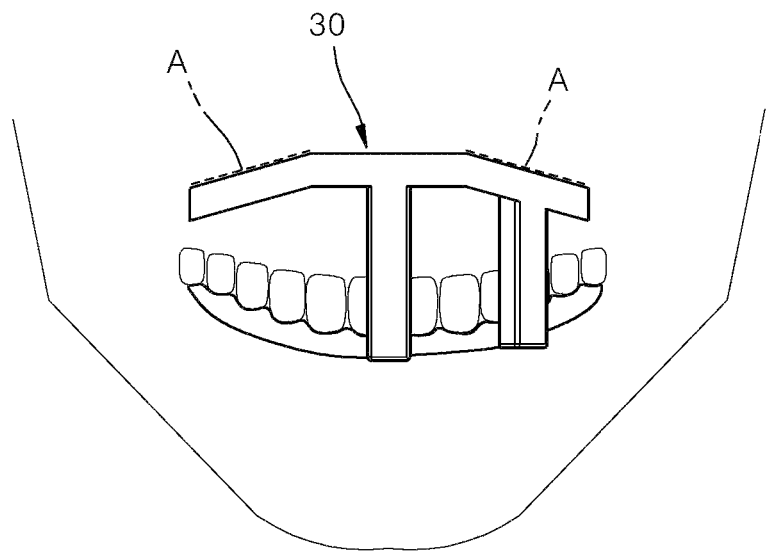
FIGS. 7 and 8 are views illustrating a use process according to the other embodiment of the present disclosure.
Figure 8:
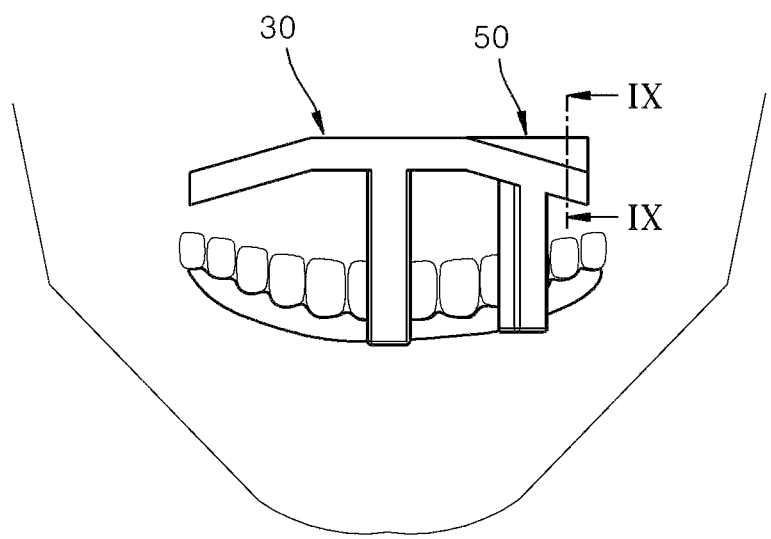
Figure 9:
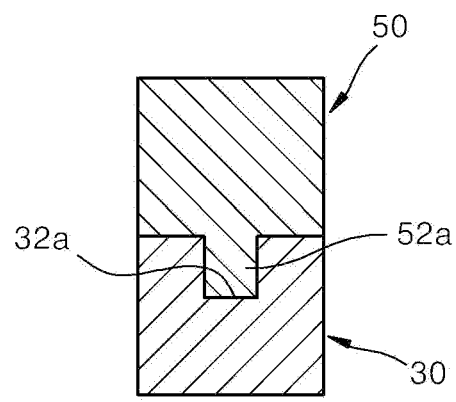
FIG. 9 is a cross-sectional view taken along line IX-IX in FIG. 8.

FIG. 4 is a front view illustrating the structure and an example use of a customizable surgical bone-cutting jigsaw puzzle-type guide device according to another embodiment of the present disclosure, FIG. 5 is an exploded perspective view according to the other embodiment of the present disclosure, FIG. 6 is an exploded perspective view at a different angle according to the other embodiment of the present disclosure, FIGS. 7 and 8 are views illustrating a use process according to the other embodiment of the present disclosure, and FIG. 9 is a cross-sectional view taken along line IX-IX in FIG. 8.

As shown in the drawings, the current embodiment further includes a sub-guide portion 50 in addition to a main guide portion 30 and connection portions 40 having structures similar to those described in the previous embodiment. As shown in FIGS. 5 and 6, the sub-guide portion 50 includes a sub-guide surface 51 and a rest surface 52.

The sub-guide surface 51, which is a portion to be brought into contact with a bone, extends lengthily along a sub-incision line B adjacent to a main incision line A as shown in FIG. 4, and the rest surface 52 is a portion to be placed on the main guide portion 30 to connect the sub-guide portion 50 and the main guide portion 30 to each other.

In the current embodiment having this configuration, as shown in FIG. 7, a first portion of the upper jawbone may be cut as a cutting blade is first guided by the main guide portion 30 along main incision lines A, and then as shown in FIG. 8, a second portion of the upper jawbone may be cut as the cutting blade is secondly guided by the sub-guide portion 50 along the sub-incision line B in a state in which the sub-guide portion 50 is placed on the main guide portion 30.

Therefore, according to the current embodiment, when it is intended to cut the upper jawbone at least twice, processes or structures for installing additional new guides are not required each time cutting is performed, but an initial installation structure may be intactly used such that a plurality of medical procedures may be performed in a relatively rapid and precise manner.

As shown in FIGS. 5, 6, and 9, a main contact surface 32 of the main guide portion 30 includes a concave coupling recess 32a, and the sub-guide portion 50 includes an insertion rib 52a configured to be inserted and fitted into the coupling recess 32a.

According to the current embodiment having this configuration, the sub-guide portion 50 may be supported by the main guide portion 30 by using its own structure without using an additional tool or a fixing process, and thus the efficiency of medical procedures may be increased.

Figure 10:
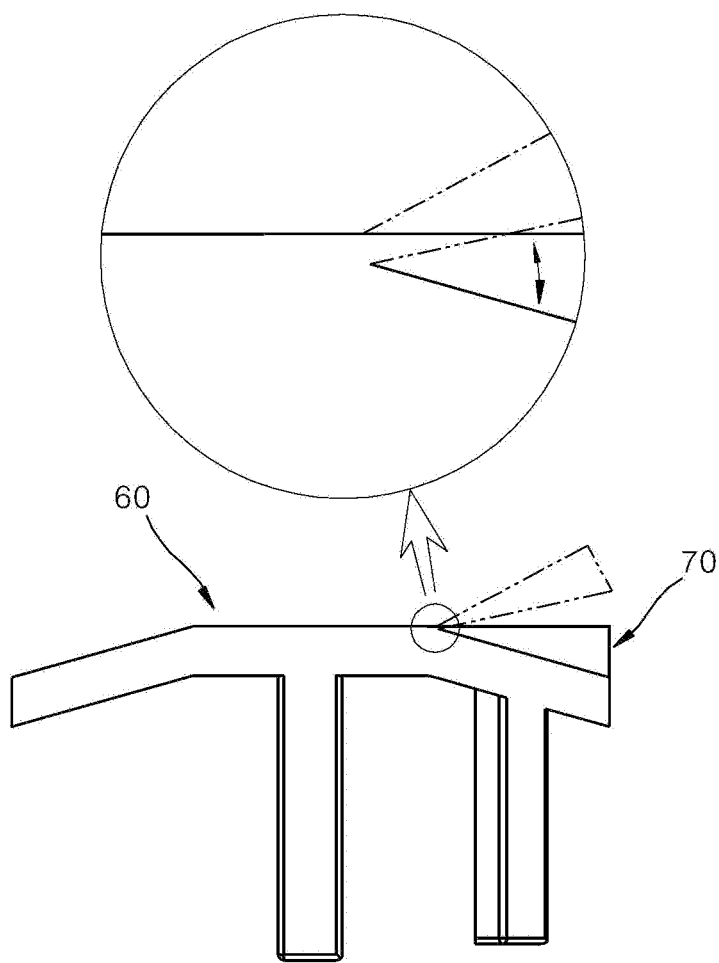
FIG. 10 is a front view according to another embodiment of the present disclosure.

FIG. 10 is a front view according to another embodiment of the present disclosure.

In the embodiment shown in FIG. 10, a side of a sub-guide portion 70 is rotatably connected to a main guide portion 60 such that when cutting is required along a main incision line, another side of the sub-guide portion 70 may be rotated around the side of the sub-guide portion 70 as shown by a two-dot chain line to ensure a space through which a cutting blade is movable along the main incision line, and then, when secondary cutting is required along a sub-incision line, the sub-guide portion 70 may be placed on the main guide portion 60 as shown by a solid line for additional cutting along the sub-incision line.

Figure 11:
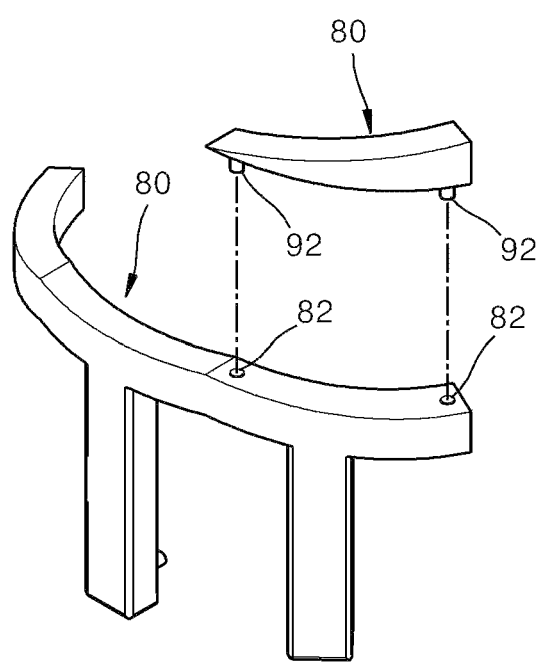
FIG. 11 is a front view according to another embodiment of the present disclosure.
Figure 12:
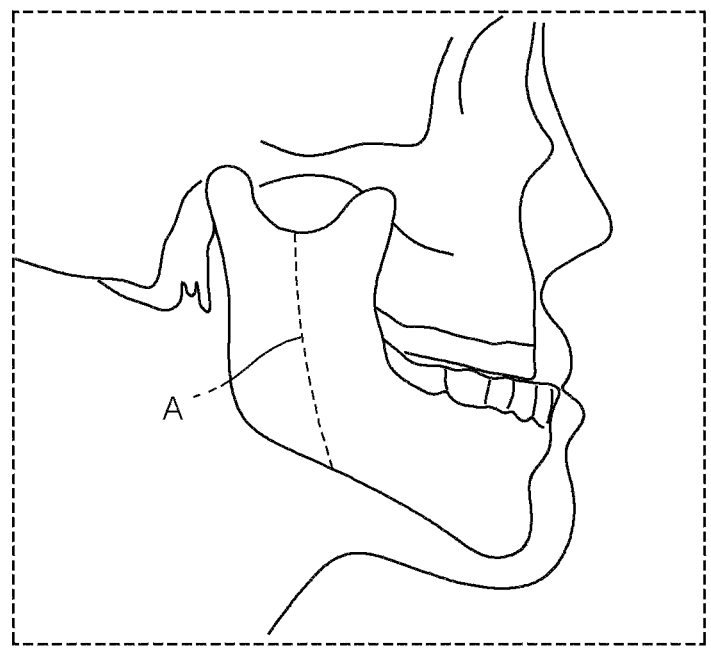
FIG. 12 is a view illustrating a process of cutting a hone in the related art.
Figure 12:
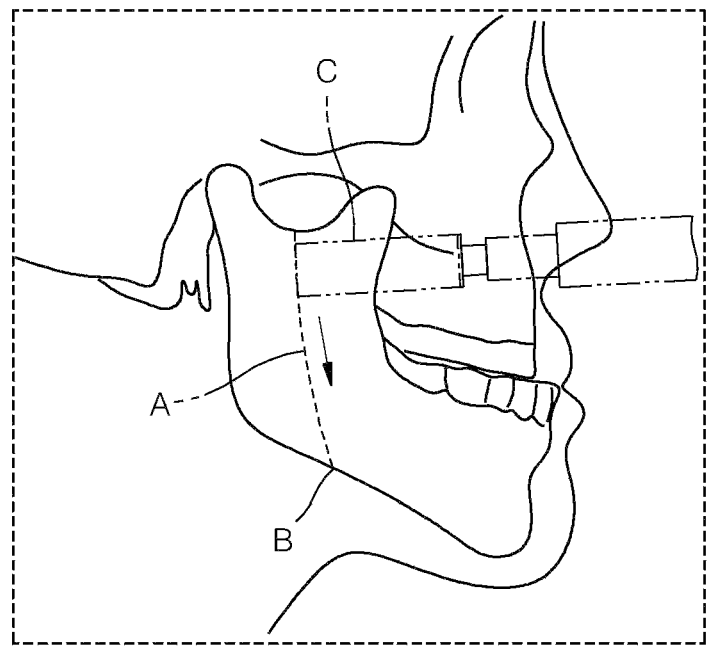

FIG. 11 is a front view according to another embodiment of the present disclosure.

In the embodiment shown in FIG. 11, a pair of coupling bosses 92 provided on both sides of a sub-guide portion 90 are configured to be respectively inserted into a pair of coupling recesses 82 of a main guide portion 80 to efficiently connect the main guide portion 70 and the sub-guide portion 800 to each other, and since a cutting blade is movable between the pair of coupling bosses 92, primary cutting along a main incision line and secondary cutting along a sub-incision line are both possible even when the main guide portion 80 and the sub-guide portion 90 are coupled to each other, thereby improving the speed and precision of medical procedures.

(Description of Customizable Surgical Bone-Cutting Guide-Traction-Suction Device)

Hereinafter, a customizable surgical bone-cutting guide-traction-suction device will be described in detail according to an embodiment of the present disclosure with reference to the accompanying drawings.

Figure 13:
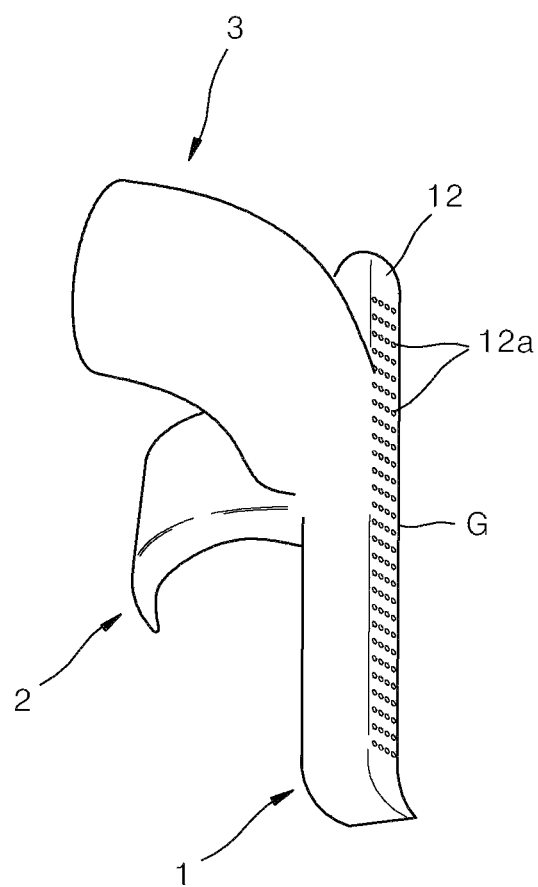
FIG. 13 is a perspective view illustrating a customizable surgical bone-cutting guide-traction-suction device according to an embodiment of the present disclosure.
Figure 14:
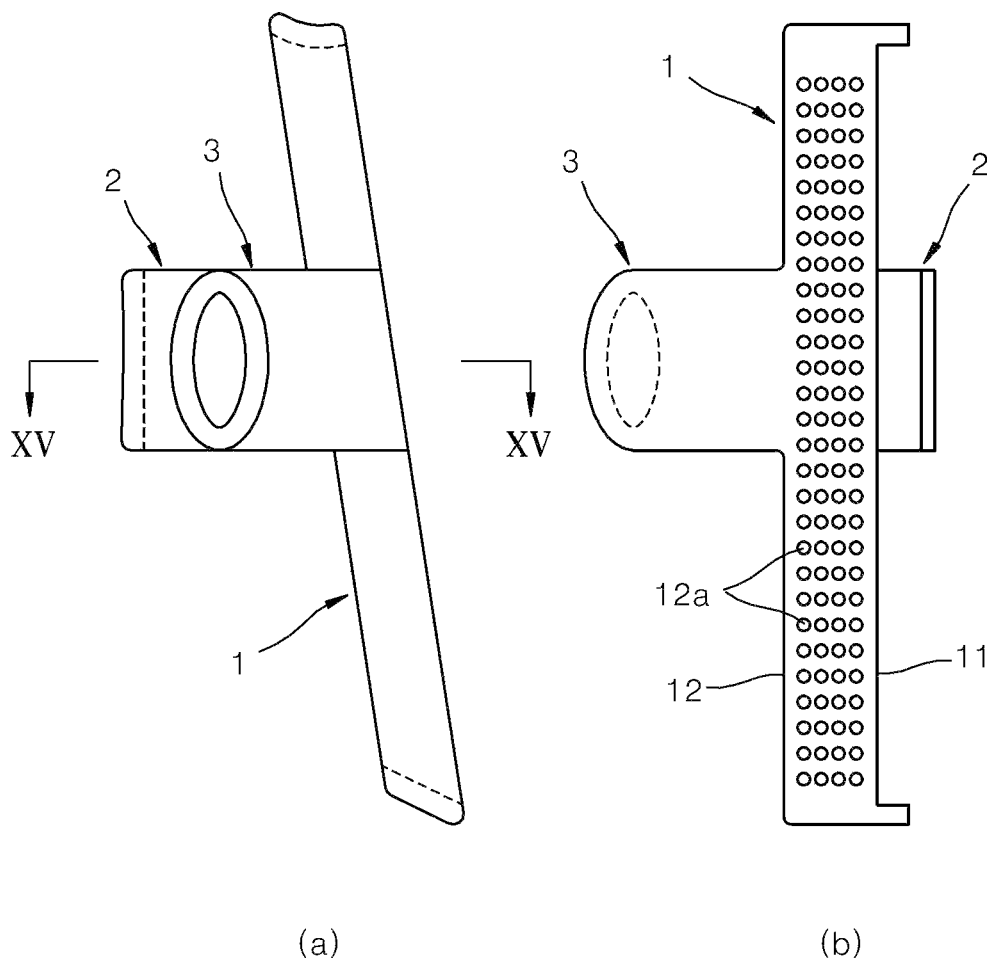
FIG. 14 is a front view and a side view according to the embodiment of the present disclosure.
Figure 15:
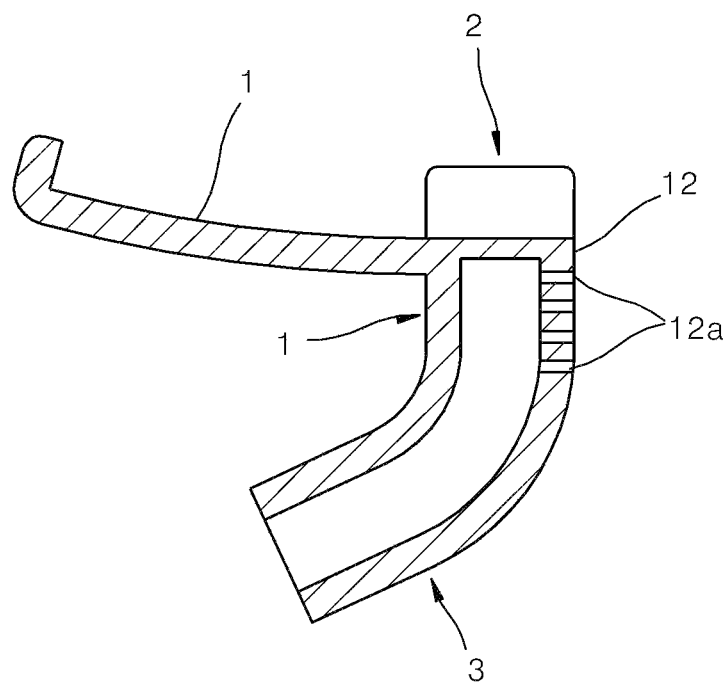
FIG. 15 is a cross-sectional view taken along line XV-XV in FIG. 3.
Figure 16:
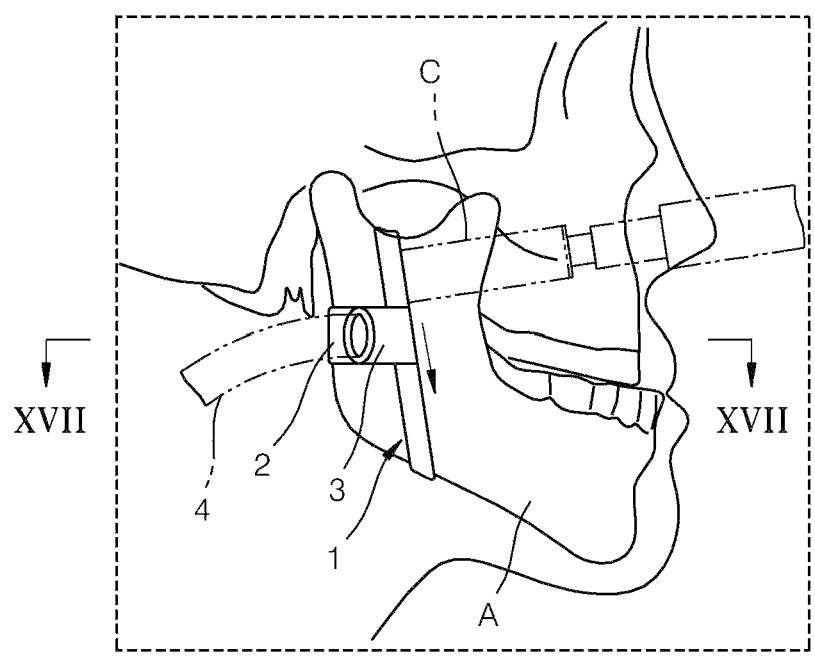
FIG. 16 is a view illustrating a use state according to the embodiment of the present disclosure.
Figure 17:
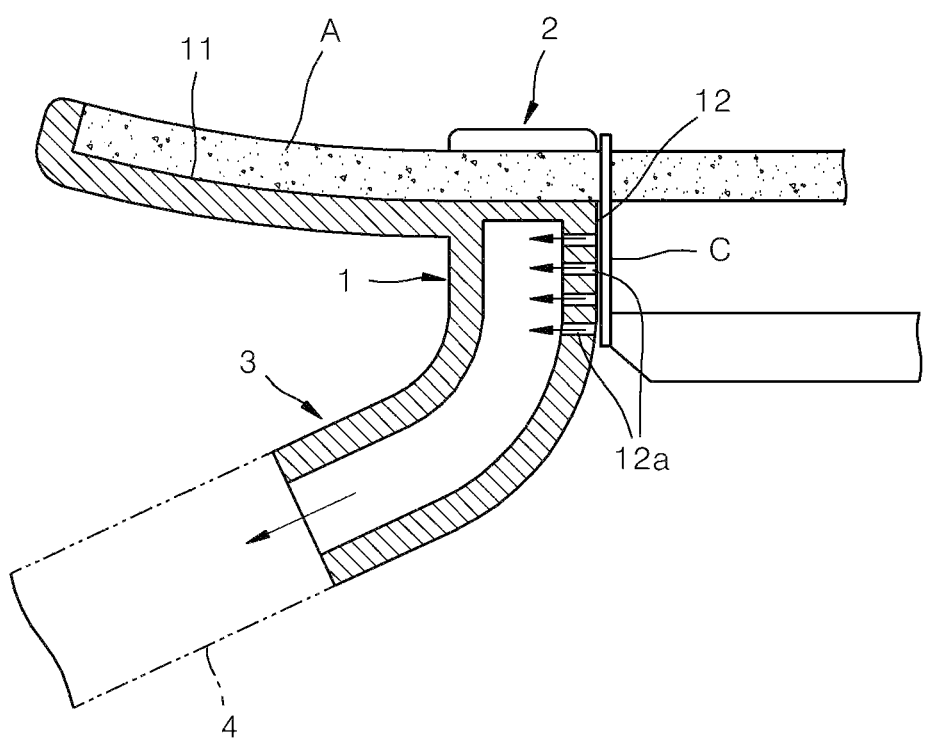
FIG. 17 is a cross-sectional view taken along line XVII-XVII in FIG. 16.

FIG. 13 is a perspective view illustrating a customizable surgical bone-cutting guide-traction-suction device according to an embodiment of the present disclosure, FIGS. 14A and 14B are a front view and a side view according to the embodiment of the present disclosure, FIG. 15 is a cross-sectional view taken along line XV-XV in FIG. 3, FIG. 16 is a view illustrating a use state according to the embodiment of the present disclosure, and FIG. 17 is a cross-sectional view taken along line XVII-XVII in FIG. 16.

As shown in FIGS. 13 to 14B, the customizable surgical bone-cutting guide-traction-suction device according to the embodiment of the present disclosure is for guiding a cutting operation in which a cutting tool such as a cutter is used to, for example, cut a protruding bone to place the bone in position. The customizable surgical bone-cutting guide-traction-suction device includes a body portion 1, a hooking portion 2, and a connection portion 3.

As shown in FIG. 15, the body portion 1 is configured to be placed in the inside of the body for contact with an object to be cut and includes a contact surface 11 and a guide surface 12. In the current embodiment, an object to be cut may be a bone, and the inside of the body may be the oral cavity in which the object is located. However, the present disclosure is not limited thereto and may be applied to cut another part of the body.

As clearly shown in FIGS. 16 and 17, the contact surface 11 has a shape corresponding to a bone for being tightly brought into contact with a surface of the bone that faces the contact surface 11, and the guide surface 12 may be brought into contact with a cutting blade C to guide the movement of the cutting blade C in a cutting direction.

As shown in FIG. 13, a guide line G is formed between the guide surface 12 and the contact surface 11 along the same line as an incision line of an object to be cut.

As shown in FIG. 16, the hooking portion 2 extends from the body portion 1 and is configured to be hooked on a side of a bone to securely hold the body portion 1 on the bone. In the current embodiment, the hooking portion 2 include a main hook configured to be hooked on the rearmost end portion of a bone, and sub-hooks configured to be hooked on upper and lower surfaces of the bone.

The connection portion 3 is connected to the body portion 1, and a connector 4 may be connected to the connection portion 3 to connect the inside and outside of the oral cavity such that the body portion 1 may be handled from the outside of the oral cavity by using the connector 4.

According to the customizable surgical bone-cutting guide-traction-suction device of the embodiment of the present disclosure, the body portion 1 is supported on a bone using the hooking portion 2 as shown in FIG. 16 to cut the bone while moving the cutting blade C along the guide surface 12 of the body portion 1, thereby preventing cutting misaligned with a required incision line, enabling rapid and precise medical procedures, and reducing clinician's fatigue. Therefore, high-quality medical services may be provided, and the effect of treatment may be improved.

In addition, although the body portion 1 and the hooking portion 2 may be formed by various methods, the body portion 1 and the hooking portion 2 may be formed in one piece by a 3D printing method to have a shape corresponding to the shape of an object to be cut which varies by person.

According to the current embodiment having the above-described configuration, a customized shape suitable for the shape of a bone which varies by person may be easily formed by a 3D printing method, and thus patient-specific medical procedures and high-quality medical services may be provided.

In the current embodiment, as clearly shown in FIG. 17, the body portion 1 has an empty space therein, and a plurality of holes 12a communicating with the empty space are formed in the guide surface 12, such that unnecessary substances may be suctioned from the body to the connection portion 3 through the holes 12a and the empty space of the body portion 1.

According to the current embodiment having this configuration, unnecessary substances such as leaking blood may be suctioned using the structure of the customizable surgical bone-cutting guide-traction-suction device without using an additional tool in the narrow oral cavity, and the view of a clinician may not be blocked by bleeding such that the clinician may perform medical procedures more easily and precisely.

Figure 18:
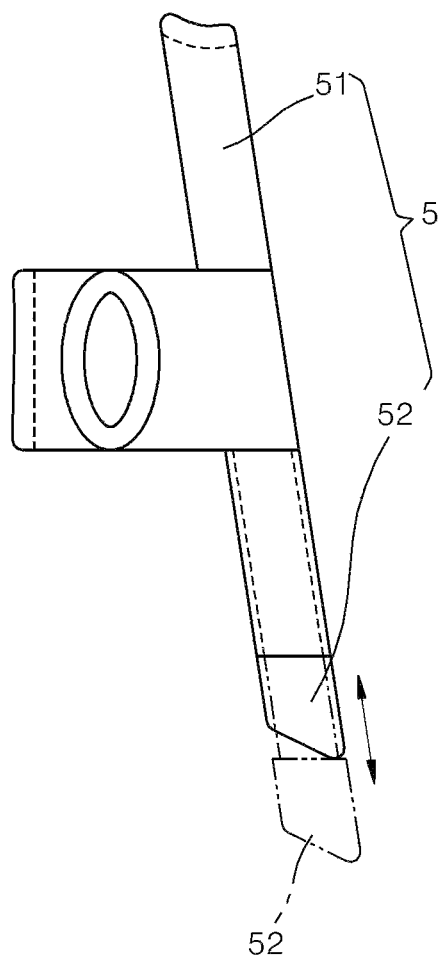
FIG. 18 is a front view illustrating a customizable surgical bone-cutting guide-traction-suction device according to another embodiment of the present disclosure.

FIG. 18 is a front view illustrating a customizable surgical bone-cutting guide-traction-suction device according to another embodiment of the present disclosure.

In the embodiment shown in FIG. 18, a body portion 5 includes a main body portion 51 and a sub-body portion 52. As in the previous embodiment, the main body portion 51 includes a contact surface and a guide surface, and the sub-body portion 52 is movably fitted to the main body portion 51 such that the guide surface may be selectively extended.

In the current embodiment having this configuration, the customizable surgical bone-cutting guide-traction-suction device may be placed in the oral cavity in a state in which the sub-body portion 52 is retracted into the main body portion 51, and then if necessary, the sub-body portion 52 may be extended from the main body portion 51 as shown by a two-dot chain line in FIG. 7. Therefore, the customizable surgical bone-cutting guide-traction-suction device of the current embodiment may be smoothly placed in the narrow oral cavity and actively handled according to different bone structures of different patients.

While various embodiments of the present disclosure have been described, the embodiments and the appended drawings cover only a portion of the scope of the present disclosure, and it will be apparent that those skilled in the art can conceive of modifications or other embodiments from the technical idea shown in the specification and the appended drawings within the scope of the present disclosure.

The invention claimed is:

1. A customizable surgical bone-cutting jigsaw puzzle-type guide device comprising: a main guide portion that comprises a main contact surface, the main guide surface, the main contact surface being lengthily formed along a required main incision line of a bone which is an object to be cut and being shaped to be brought into contact with the bone, the main guide surface forming a guide line between the main contact surface and the main guide surface along a same line as the incision line and being shaped to be brought into contact with a cutting blade for cutting the bone to guide a movement of the cutting blade; and a connection portion that extends from the main guide portion and is configured to be connected to a side of the bone such that the main guide portion is supported on the bone, the connection portion being configured to be detachably attached to the side of the bone, wherein when the bone to be cut corresponds to a maxillofacial bone including a maxilla and the side of the bone to which the connection portion is attached corresponds to a medical guide coupled to a tooth in an oral cavity, the connection portion comprises a coupling boss configured to be press fitted into a hole formed in the medical guide.

2. A customizable surgical bone-cutting jigsaw puzzle-type guide device comprising: a main guide portion that comprises a main contact surface, the main guide surface, 5 the main contact surface being lengthily formed along a required main incision line of a bone which is an object to be cut and being shaped to be brought into contact with the bone, the main guide surface forming a guide line between the main contact surface and the main guide surface along a same line as the incision line and being shaped to be brought into contact with a cutting blade for cutting the bone to guide a movement of the cutting blade; and a connection portion that extends from the main guide portion and is configured to be connected to a side of the bone such that the main guide portion is supported on the bone, the connection portion being configured to be detachably attached to the side of the bone, and further comprising a sub-guide portion that comprises a sub-contact surface lengthily formed along a sub-incision line adjacent to the main incision line and shaped to be brought into contact with the bone, a sub-guide surface configured to guide a movement of the cutting blade, and a rest surface configured to be placed on the main guide portion.

3. The customizable surgical bone-cutting jigsaw puzzle-type guide device of claim 2, wherein the main contact surface of the main guide portion comprises a concave coupling recess, and the sub-guide portion comprises an insertion rib configured to be inserted and fitted into the coupling recess for being supported on the main guide portion, such that the bone is primarily cut along the main incision line by using the cutting blade and is then secondarily cut along the sub-incision line in a state in which the sub-guide portion is supported on the main guide portion.

4. The customizable surgical bone-cutting jigsaw puzzle-type guide device of claim 2, wherein a side of the sub-guide portion is rotatably connected to the main guide portion such that another side of the sub-guide portion is rotated around the side of the sub-guide portion to ensure a space for the cutting blade to move along the main incision line and is placed on the main guide portion to move the cutting blade along the sub-incision line.

* * * * *